(12) United States Patent
Birudaraj et al.

(10) Patent No.: US 7,393,839 B2
(45) Date of Patent: Jul. 1, 2008

(54) POLYMORPHIC ANTIVIRAL NUCLEOSIDE COMPOUNDS

(75) Inventors: Kondamraj Birudaraj, Belmont, CA (US); Anthony Prince, deceased, late of Old Lyme CT (US); by Keith McCarthy, legal representative, Old Lyme, CT (US)

(73) Assignee: Roche Palo Alto LLC, Palo Alto, CA (US)

( * ) Notice: Subject to any disclaimer, the term of this patent is extended or adjusted under 35 U.S.C. 154(b) by 513 days.

(21) Appl. No.: 10/939,648

(22) Filed: Sep. 13, 2004

(65) Prior Publication Data
US 2005/0130915 A1    Jun. 16, 2005

Related U.S. Application Data

(60) Provisional application No. 60/502,105, filed on Sep. 11, 2003.

(51) Int. Cl.
*A01N 43/04* (2006.01)
*A61K 31/70* (2006.01)
*A61K 38/21* (2006.01)

(52) U.S. Cl. .................. 514/42; 514/43; 514/885; 424/85.4

(58) Field of Classification Search ............ 514/42, 514/43, 885; 424/85.4
See application file for complete search history.

(56) References Cited

U.S. PATENT DOCUMENTS

| | | | |
|---|---|---|---|
| 6,277,830 B1* | 8/2001 | Ganguly et al. | 514/43 |
| 6,495,677 B1* | 12/2002 | Ramasamy et al. | 536/28.6 |
| 2004/0121969 A1 | 6/2004 | Hendricks et al. | |

FOREIGN PATENT DOCUMENTS

| | | |
|---|---|---|
| WO | WO 01/45509 A1 | 6/2001 |
| WO | WO 01/68034 A2 | 9/2001 |
| WO | WO 2004/052905 A2 | 6/2004 |

\* cited by examiner

*Primary Examiner*—Shaojia Anna Jiang
*Assistant Examiner*—Traviss McIntosh
(74) *Attorney, Agent, or Firm*—Brian L. Buckwalter (57) ABSTRACT

The present invention relates to the polymorphic crystalline hydrochloride salts of a nucleoside valinate ester according to formula Ib, methods of treating diseases mediated by Hepatitis C Virus and pharmaceutical composition containing Ib

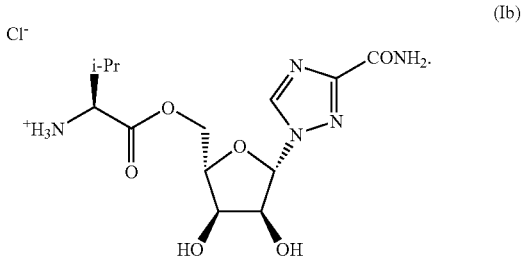

(Ib)

15 Claims, 7 Drawing Sheets

*FIGURE 3B* Form B Polymorph

*FIGURE 3A* Form A Polymorph

*Figure 4b*
Thermal Gravimetric Analysis

*Figure 4a*
Differential Scanning Calorimetry

*Figure 5b*
Thermal Gravimetric Analysis

*Figure 5a*
Differential Scanning Calorimetry

POLYMORPHIC ANTIVIRAL NUCLEOSIDE COMPOUNDS

CROSS REFERENCE TO PRIOR APPLICATION

This application claims benefit under Title 35 U.S.C. 119 (e) of U.S. Provisional Application No. 60/502,105, filed Sep. 11, 2003, which is hereby incorporated by reference in its entirety.

FIELD OF THE INVENTION

The present invention relates to polymorphic crystalline forms of 2-(S)-amino-3-methyl-butyric acid 5S-(3-carbamoyl-[1,2,4]triazol-1-yl)-3R,4S-dihydroxy-tetrahydrofuran-2S-yl methyl ester, monohydrochloride (Ib) with improved stability and physical properties which facilitate manufacturing, handling and formulating I.

BACKGROUND OF THE INVENTION

Hepatitis C virus (HCV) is responsible for a large proportion of the chronic liver disease worldwide and accounts for 70% of cases of chronic hepatitis in industrialized countries. The global proportion of hepatitis C is estimated to average 3% (ranging from 0.1% to 5.0%); there are an estimated 170 million chronic carriers throughout the world. There is a continuing need for effective therapeutic agents against HCV. Standard therapy for hepatitis C infection presently consists of combination therapy with an antiviral, ribavirin, and an immunomodulatory interferon derivative.

WO 01/45509 (J. Lau et al.) discloses L-nucleosides with in vivo antiviral activity against HCV. Levovirin (1-(3S,4R-dihydroxy-5S-hydroxymethyl-tetrahydro-furan-2S-yl)-1H-[1,2,4]triazole-3-carboxylic acid amide; Ia), is the L-isomer of the antiviral nucleoside ribavirin (II). Unlike ribavirin, levovirin does not have direct detectable antiviral activity; however, levovirin stimulates immune responses by enhancing antiviral Th1 cytokine expression. Levovirin appears to lack toxicity associated with ribavirin.

Ia: R = H (L-isomer);
Ib: R = CO—CH(i-Pr)NH$_3^+$Cl$^-$

II: R = H (D-isomer)

While nucleoside derivatives frequently possess high levels of biological activity, their clinical utility is often hampered by suboptimal physical properties and limited bioavailability requiring large doses at frequent intervals to maintain therapeutically effective levels. Chemical modification of the nucleoside can alter the physicochemical properties of the compound and improve the efficiency and selectivity of drug delivery.

Esters of neutral amino acid acids have been found to actively transported across the intestinal mucosa by amino acid transporters. Colla et al. (*J. Med. Chem.* 1983 26:602-04) disclose the preparation of water soluble ester derivatives of acyclovir. L. M. Beauchamp et al. (*Antiviral Chem. & Chemother.* 1992 3(3):157-64) disclose eighteen amino acid esters of the antiherpetic drug acyclovir and identified the L-valyl ester of acyclovir as the best prodrug among the esters investigated.

EP 0 375 329 (L. M. Beauchamp) disclosed the preparation of the bis-iso-leucine ester of gangciclovir. U.S. Pat. No. 6,083,953 (J. J. Nestor et al.) discloses a crystalline from of 2-(2-amino-1,6-dihydro-6-oxo-purin-9-yl)methoxy-3-hydroxy-1-propanyl-L-valinate hydrochloride WO 00/23454 (A. K. Ganguly et al.) disclose bioreversible prodrugs of ribavirin II. Compounds in which the 5-hydroxy of II is esterified to natural and unnatural amino acids are disclosed. U.S. Pat. No. 6,423,695 (R. Tam et al.) disclose methods of treating a patient with a virus infection by administering amidine prodrugs of ribavirin.

WO 01/68034 (G. Wang et al.) disclose bioreversible phosphorylated and non-phosphorylated prodrugs of levovirin. 5-Acyl and 2,3,5-triacyl compounds are disclosed and 5-amino acid esters are also described generically. U.S. Ser. No. 60/432,108 discloses acylated prodrugs of levovirin.

Salts of acidic and basic compounds can alter or improve the physical properties of a parent compound. These salt forming agents, however, must be identified empirically by the pharmaceutical chemist since there is no reliable method to predict the influence of a salt species on the behavior of a parent compound in dosage forms. Effective screening techniques, which potentially could simplify the selection process, are unfortunately absent (G. W. Radebaugh and L. J. Ravin Preformulation. In, *Remington: The Science and Practice of Pharmacy*; A. R. Gennaro Ed.; Mack Publishing Co. Easton, Pa., 1995; pp 1456-1457).

Polymorphism is the ability of any element or compound to crystallize as more than one distinct crystalline species. Different polymorphic forms of salts are frequently encountered among pharmaceutically useful compounds. Physical properties including solubility, melting point, density, hardness, crystalline shape and stability can be quite different for different polymorphic forms of the same chemical compound.

Polymorphic forms are characterized by scattering techniques, e.g., x-ray diffraction powder pattern, by spectroscopic methods, e.g., infa-red, $^{13}$C nuclear magnetic resonance spectroscopy and by thermal techniques, e.g, differential scanning calorimetry or differential thermal analysis. The compound of this invention is best characterized by the X-ray powder diffraction pattern determined in accordance with procedures which are known in the art. For a discussion of these techniques see J. Haleblian, *J. Pharm. Sci.* 1975 64:1269-1288, and J. Haleblain and W. McCrone, *J. Pharm. Sci.* 1969 58:911-929. Although the intensities of peaks in the x-ray powder diffraction patterns of different batches of the valinate ester Ia may vary slightly, the peaks and the peak locations are characteristic for a specific polymorphic form.

The problem which must be solved is to identify a suitable salt and/or polymorph which (i) possesses adequate chemical stability during the manufacturing process, (ii) is efficiently prepared, purified and recovered, (ii) provides acceptable solubility in pharmaceutically acceptable solvents, (iii) is amenable to manipulation (e.g. flowability and particle size) and formulation with negligible decomposition or change of the physical and chemical characteristics of the compound, (iv) exhibits acceptable chemical stability in the formulation. In addition, salts which contribute minimally to the molar weight so that the resulting material comprises a high molar percent of the active ingredient are highly desirable since the quantity of material which must be formulated and administered to produce a therapeutically effective dose is minimized. These oft conflicting requirements make identification suitable salts a challenging and important problem which must be solved by the skilled pharmaceutical scientist before drug development can proceed in earnest.

SUMMARY OF THE INVENTION

This invention relates to two polymorphic crystalline forms, Form A and Form B, of 2-(S)-amino-3-methyl-butyric acid 5S-(3-carbamoyl-[1,2,4]triazol-1-yl)-3R,4S-dihydroxy-tetrahydrofuran-2S-yl methyl ester, monohydrochloride Ib, methods to prepare polymorphic crystalline forms of (Ib), pharmaceutical compositions containing the polymorphic forms of Ib, and methods to treat diseases mediated by the Hepatitis C Virus using a polymorphic form of Ib.

(Ib)

BRIEF DESCRIPTION OF THE FIGURES

The numerous objects and advantages of the present invention can be directly understood by those skilled in the art by reference to the accompanying figures in which.

DETAILED DESCRIPTION OF THE INVENTION

New crystalline forms of 2-(S)-amino-3-methyl-butyric acid 5S-(3-carbamoyl-[1,2,4]triazol-1-yl)-3R,4S-dihydroxy-tetrahydrofuran-2S-yl methyl ester, monohydrochloride (Ib) have been identified with superior chemical and physical properties which facilitate manufacturing and formulation of the compound. In an embodiment of the present invention there is provided a crystalline form of a compound according to formula Ib.

In another embodiment of the present invention there is provided a crystalline polymorphic hemihydrate (Form A) of a compound according to formula Ib with an x-ray powder diffraction trace having a D-spacing substantially as in Table 1.

TABLE 1

| D-space | $I/I_o \times 100$ |
|---------|--------------------|
| 9.1200  | 35.42              |
| 6.4204  | 39.48              |
| 5.6103  | 33.43              |
| 4.9820  | 68.77              |
| 4.8788  | 41.38              |
| 4.5547  | 66.82              |
| 4.5098  | 36.84              |
| 4.4227  | 55.89              |
| 4.3497  | 43.98              |
| 4.3019  | 35.58              |
| 4.0573  | 50.71              |
| 3.7012  | 100.0              |
| 3.5856  | 34.16              |
| 3.3832  | 53.52              |
| 3.2480  | 48.14              |
| 2.6876  | 40.44              |
| 2.5744  | 26.15              |

Figure 2:
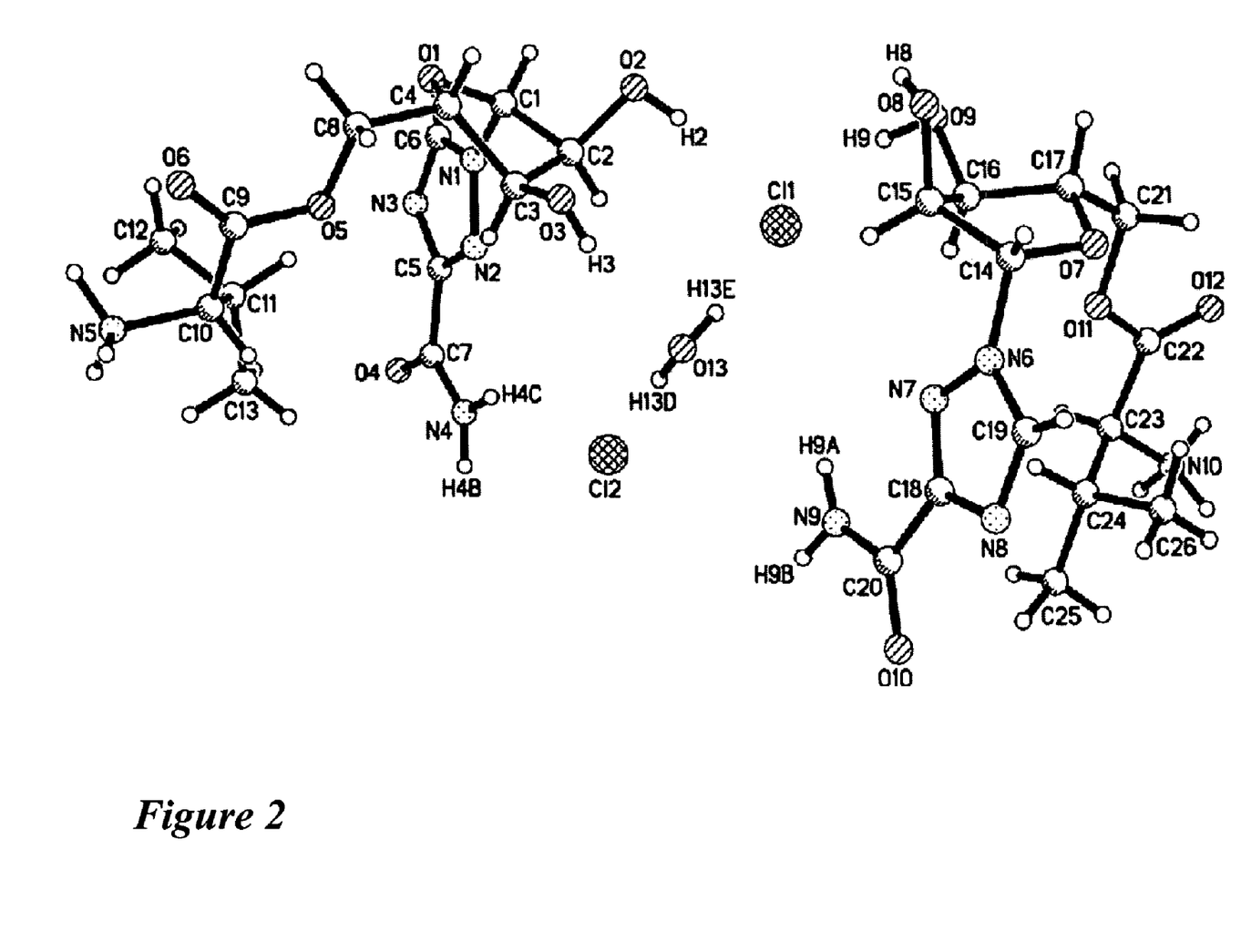
FIG. 2 shows the single crystal x-ray diffraction structure of the Form A polymorph. Atomic coordinates are provided in Table 2.

In another embodiment of the present invention there is provided a crystalline polymorphic hemihydrate of a compound according to formula Ib with a single crystal x-ray atomic coordinates essentially as listed in Table 4. FIG. 2 is computer-generated representation of the crystal data.

In another embodiment of the present invention there is provided a crystalline polymorphic hemihydrate of a compound according to formula Ib with a density of about 0.35 g/cm³.

In another embodiment of the present invention there is provided a process for preparing a crystalline polymorphic hemihydrate (Form A) of a compound according to formula Ib with a x-ray powder diffraction pattern substantially as shown in Table 1 which process comprises crystallizing said compound from a mixture of iso-propanol and water optionally further comprising 37% hydrochloric acid.

In another embodiment of the present invention there is provided a crystalline polymorphic hemihydrate of a compound according to formula Ib prepared process comprising crystallizing said compound from a mixture of iso-propanol and water optionally further comprising 37% hydrochloric acid.

In another embodiment of the present invention there is provided a method of treating a disease mediated by HCV comprising administering to a patient in need thereof, a therapeutically effective amount of the Form A polymorph of a compound according to formula Ib and an x-ray powder diffraction trace having a D-spacing substantially as in Table 1.

In another embodiment of the present invention there is provided a method of treating a disease mediated by HCV comprising administering to a patient in need thereof, a therapeutically effective amount of the Form A polymorph of a compound according to formula Ib and an x-ray powder diffraction trace having a D-spacing substantially as in Table 1 in combination therapy with an immune system modulator and/or an antiviral compound.

In another embodiment of the present invention there is provided a method of treating a disease mediated by HCV comprising administering to a patient in need thereof, a therapeutically effective amount of the Form A polymorph of a compound according to formula Ib and an x-ray powder diffraction trace having a D-spacing substantially as in Table 1 in combination therapy with an interferon or chemically derivatized interferon.

In another embodiment of the present invention there is provided a pharmaceutical composition comprising a crystalline polymorphic hemihydrate (Form A) of a compound according to formula Ib with an x-ray powder diffraction trace having a D-spacing substantially as in Table 1 in admixture with al least one pharmaceutically acceptable carrier, diluent or excipient.

In another embodiment of the present invention there is provided a crystalline polymorphic hydrate (Form B) of a compound according to formula Ib with an x-ray powder diffraction trace having a D-spacing substantially as in Table 2

TABLE 2

| D-space | $I/I_o \times 100$ |
|---|---|
| 9.8689 | 18.94 |
| 8.2942 | 25.69 |
| 7.3390 | 42.22 |
| 6.8145 | 34.08 |
| 6.0572 | 44.64 |
| 5.6245 | 100.0 |
| 5.1887 | 23.52 |
| 4.9482 | 22.35 |
| 4.5828 | 32.87 |
| 4.4324 | 24.86 |
| 4.3275 | 34.15 |
| 4.0081 | 31.11 |
| 3.7143 | 50.33 |
| 3.4204 | 58.91 |
| 3.3062 | 47.28 |

In another embodiment of the present invention there is provided a process for preparing a crystalline polymorphic hydrate (Form B) of a compound according to formula Ib with a x-ray powder diffraction pattern substantially as shown in Table 2 which process comprises crystallizing said compound from water maintained at a temperature at or below 2 to 4° C. for a period of at least 2 to 3 days.

In another embodiment of the present invention there is provided a crystalline polymorphic hydrate of a compound according to formula Ib prepared by a process comprising crystallizing said compound from water.

In another embodiment of the present invention there is provided a method of treating a disease mediated by HCV comprising administering to a patient in need thereof, a therapeutically effective amount of the Form B polymorph of a compound according to formula Ib and an x-ray powder diffraction trace having a D-spacing substantially as in Table 2.

In another embodiment of the present invention there is provided a method of treating a disease mediated by HCV comprising administering to a patient in need thereof, a therapeutically effective amount of the Form B polymorph of a compound according to formula Ib and an x-ray powder diffraction trace having a D-spacing substantially as in Table 2 in combination therapy with an immune system modulator and/or an antiviral compound.

In another embodiment of the present invention there is provided a method of treating a disease mediated by HCV comprising administering to a patient in need thereof, a therapeutically effective amount of the Form B polymorph of a compound according to formula Ib and an x-ray powder diffraction trace having a D-spacing substantially as in Table 2 in combination therapy with an interferon or chemically derivatized interferon.

In another embodiment of the present invention there is provided a pharmaceutical composition 5 comprising a containing a crystalline polymorphic hydrate (Form B) of a compound according to formula Ib with an x-ray powder diffraction trace having a D-spacing substantially as in Table 2 in admixture with al least one pharmaceutically acceptable carrier, diluent or excipient.

Preparation and Properties

Figure 1:
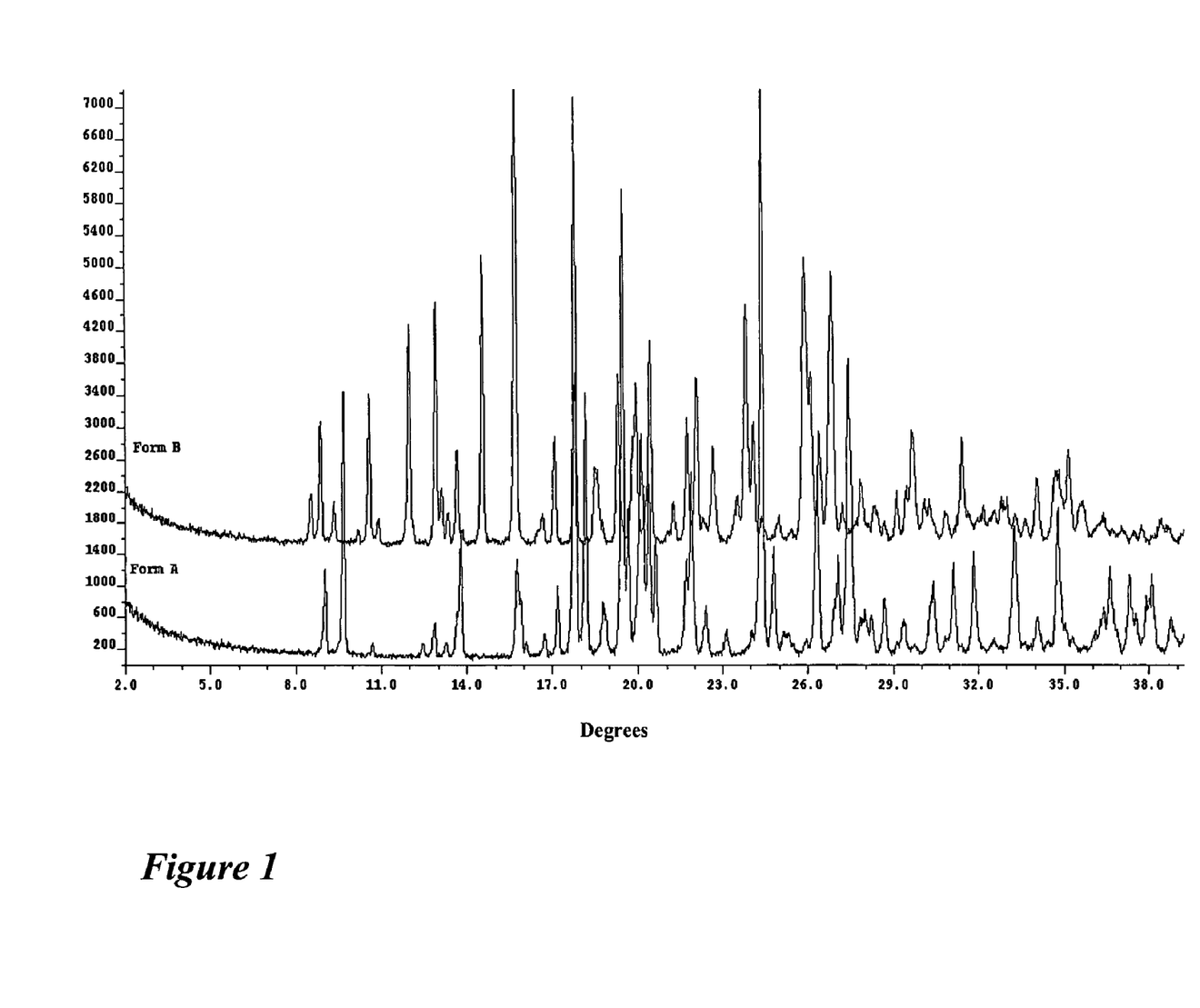
FIG. 1 shows a superposition of the x-ray powder diffraction of the Form A and Form B polymorphic form of Ib. The diffraction data for Form A and Form B is tabulated in Table 1 and 3 respectively in the specification.
Figure 3A:
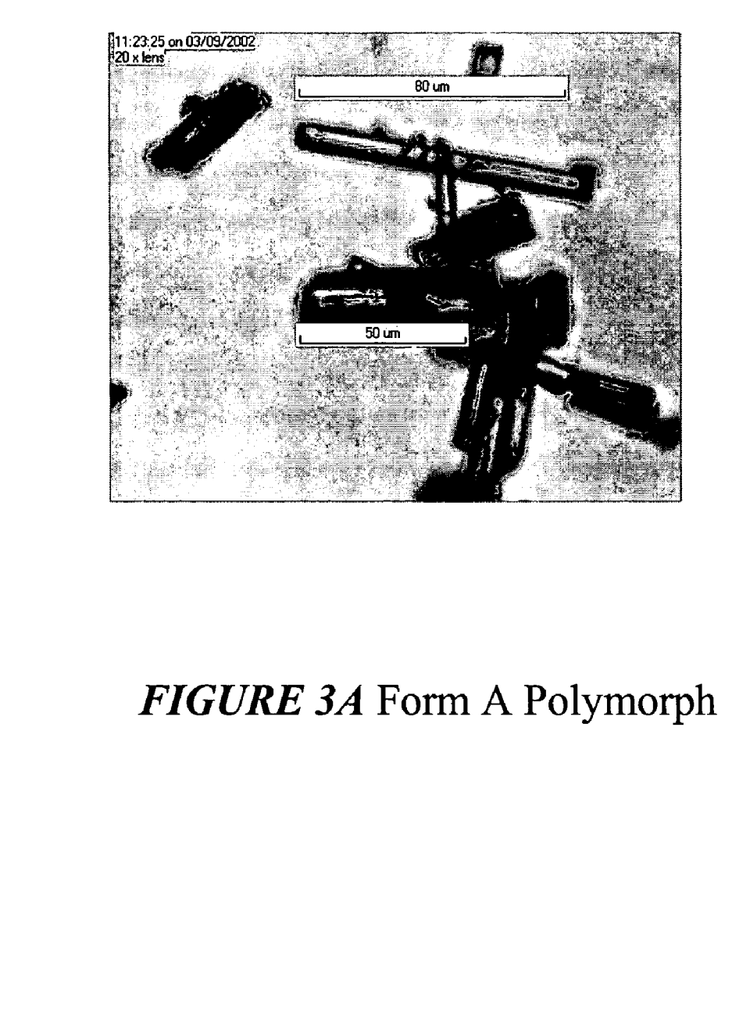
FIG. 3 shows a photograph of Form A and Form B crystals. Microscopic observations were made with Olympus BX50 and Olympus PH polarized light microscopes in conjunction with a Mettler FP 82 hot stage equipped with a Mettler FP 80 controller.

Form A was obtained initially by crystallization from aqueous iso-propanol optionally containing 37% hydrochloric acid. Form A crystals are rod shaped (FIG. 3a). The water content of Form A crystals ranged from 1.88 to 2.68% by Karl Fischer titration corresponding to 0.4 to 0.6 moles of water per mole of Ib. The bulk and tapped densities of Ib were determined to be 0.35 g/cm$^3$ and 0.58 g/cm$^3$, respectively. The powder x-ray diffraction pattern of Form A is shown in FIG. 1 and values are tabulated in Table 3.

TABLE 3

| degrees | D-space | relative intensity | degrees | D-space | relative intensity |
|---|---|---|---|---|---|
| 9.0306 | 9.7844 | 14.93 | 26.3206 | 3.3832 | 53.52 |
| 9.6900 | 9.1200 | 35.42 | 27.0656 | 3.2918 | 19.45 |
| 10.6938 | 802661 | 4.69 | 27.4375 | 3.2480 | 58.14 |
| 12.8756 | 6.8699 | 13.93 | 27.9200 | 3.1929 | 7.33 |
| 13.3000 | 6.6516 | 6.80 | 28.2512 | 3.1563 | 5.48 |
| 13.7813 | 6.4204 | 39.48 | 27.7081 | 3.1071 | 8.02 |
| 15.7831 | 5.6103 | 33.43 | 29.4144 | 3.0340 | 8.62 |
| 16.7394 | 5.2919 | 6.62 | 29.7600 | 2.9996 | 4.25 |
| 17.2000 | 5.1512 | 7.66 | 30.4231 | 2.9357 | 17.65 |
| 17.7887 | 4.9820 | 68.77 | 30.9306 | 2.8887 | 6.81 |
| 18.1681 | 4.8788 | 41.38 | 31.1600 | 2.8679 | 22.18 |
| 18.8113 | 4.7134 | 16.55 | 31.9000 | 2.8031 | 16.42 |
| 19.4731 | 4.5547 | 66.82 | 33.3094 | 2.6876 | 40.44 |
| 19.6688 | 4.5098 | 36.84 | 34.1125 | 2.6262 | 8.11 |
| 20.0600 | 4.4227 | 55.89 | 34.4200 | 2.6034 | 5.10 |
| 20.4006 | 4.3497 | 43.98 | 34.8200 | 2.5744 | 26.15 |
| 20.6294 | 4.3019 | 35.58 | 35.1000 | 2.5545 | 7.98 |
| 21.4400 | 4.1411 | 4.32 | 36.3819 | 2.4674 | 4.70 |
| 21.8881 | 4.0573 | 50.71 | 36.6625 | 2.4491 | 11.75 |
| 22.4181 | 3.9626 | 15.32 | 37.3375 | 2.4064 | 9.31 |
| 23.1313 | 3.8420 | 10.87 | 37.5531 | 2.3943 | 4.33 |
| 24.0238 | 3.7012 | 3.75 | 37.9831 | 2.3670 | 11.45 |
| 24.3913 | 3.6463 | 100.0 | 38.1000 | 2.3600 | 12.30 |
| 24.8106 | 3.5856 | 34.16 | 38.7831 | 2.3200 | 6.07 |
| 25.3219 | 3.5144 | 8.91 | 39.2200 | 2.2951 | 4.32 |

The hemihydrate was further characterized with a single crystal x-ray analysis. The structure (FIG. 2) contains one molecule of water between and two chloride atoms between two molecules of the valinate ester of levovirin. The atomic coordinates are tabulated in Table 4.

TABLE 4

Atomic coordinates (×10⁴) and equivalent isotropic displacement parameters ($Å^2 × 10^3$) for Form A of Ib.

| | x | y | z | U(eq) | | x | y | z | U(eq) |
|---|---|---|---|---|---|---|---|---|---|
| Cl(1) | 8746(1) | 8772(1) | 3214(1) | 29(1) | Cl(2) | 4337(1) | 7796(1) | 2768(1) | 25(1) |
| C(1) | 8687(2) | 7008(1) | 6432(2) | 18(1) | C(14) | 11235(2) | 8965(1) | −1389(2) | 17(1) |
| C(2) | 8690(2) | 7291(1) | 5035(2) | 17(1) | C(15) | 11243(2) | 8693(1) | 16(2) | 17(1) |
| C(3) | 8434(2) | 6632(1) | 4217(2) | 19(1) | C(16) | 10963(2) | 9359((1) | 810(2) | 17(1) |
| C(4) | 9276(2) | 6098(1) | 5024(2) | 19(1) | C(17) | 11762(2) | 9898(1) | −1(2) | 17(1) |
| C(5) | 4955(2) | 7149(1) | 7211(2) | 18(1) | C(18) | 7490(2) | 8857(1) | −2164(2) | 17(1) |
| C(6) | 6915(2) | 7088(1) | 8326(2) | 18(1) | C(19) | 9413(2) | 8859(1) | −3274(2) | 19(1) |
| C(7) | 3358(2) | 7239(1) | 6862(2) | 19(1) | C(20) | 5898(2) | 8825(1) | −1815(2) | 17(1) |
| C(8) | 8850(2) | 5352(1) | 4814(2) | 24(1) | C(21) | 11261(2) | 10634(1) | 179(2) | 21(1) |
| C(9) | 6719(2) | 4664(1) | 5104(2) | 18(1) | C(22) | 9088(2) | 11295(1) | −17(2) | 18(1) |
| C(10) | 5057(2) | 4711(1) | 5279(2) | 18(1) | C(23) | 7418(2) | 11254(1) | −138(2) | 17(1) |
| C(11) | 4573(2) | 5165(1) | 6448(2) | 21(1) | C(24) | 6847(2) | 10747(1) | −1189(2) | 20(1) |
| C(12) | 4725(2) | 4773(1) | 7744(1) | 30(1) | C(25) | 5164(1) | 10780(1) | −1296(2) | 26(1) |
| C(13) | 3010(2) | 5434(1) | 6239(2) | 26(1) | C(26) | 7564(2) | 10867(1) | −2511(2) | 30(1) |
| O(1) | 9023(1) | 6287(1) | 6364(1) | 22(1) | O(7) | 11560(1) | 9687(1) | −1339(1) | 19(1) |
| O(2) | 10098(1) | 7585(1) | 4803(1) | 22(1) | O(8) | 12683(1) | 8438(1) | 289(1) | 20(1) |
| O(3) | 8995(2) | 6642(1) | 2942(1) | 27(1) | O(9) | 11606(1) | 9330(1) | 2076(1) | 21(1) |
| O(4) | 2417(1) | 7239(1) | 7729(1) | 27(1) | O(10) | 4940(1) | 8842(1) | −2681(1) | 24(1) |
| O(5) | 7272(1) | 5301(1) | 5010(1) | 28(1) | O(11) | 9666(1) | 10660(1) | 22(1) | 22(1) |
| O(6) | 7405(1) | 4136(1) | 5026(1) | 22(1) | O(12) | 9772(1) | 11826(1) | 60(1) | 24(1) |
| N(1) | 7250(1) | 7087(1) | 7046(1) | 17(1) | N(6) | 9782(1) | 8878(1) | −1997(1) | 17(1) |
| N(2) | 5989(2) | 7123(1) | 6315(1) | 18(1) | N(7) | 8543(2) | 8882(1) | −1263(1) | 19(1) |
| N(3) | 5467(2) | 7117(1) | 8473(1) | 19(1) | N(8) | 7968(2) | 8845(1) | −3432(1) | 20(1) |
| N(4) | 3060(1) | 7314(1) | 5602(1) | 23(1) | N(9) | 5625(2) | 8781(1) | −549(1) | 24(1) |
| N(5) | 4480(2) | 3990(1) | 5347(1) | 17(1) | N(10) | 6858(2) | 11973(1) | −323(1) | 18(1) |
| | | | | | O(13) | 7403(2) | 7598(1) | 1411(2) | 42(1) |

Figure 4A:
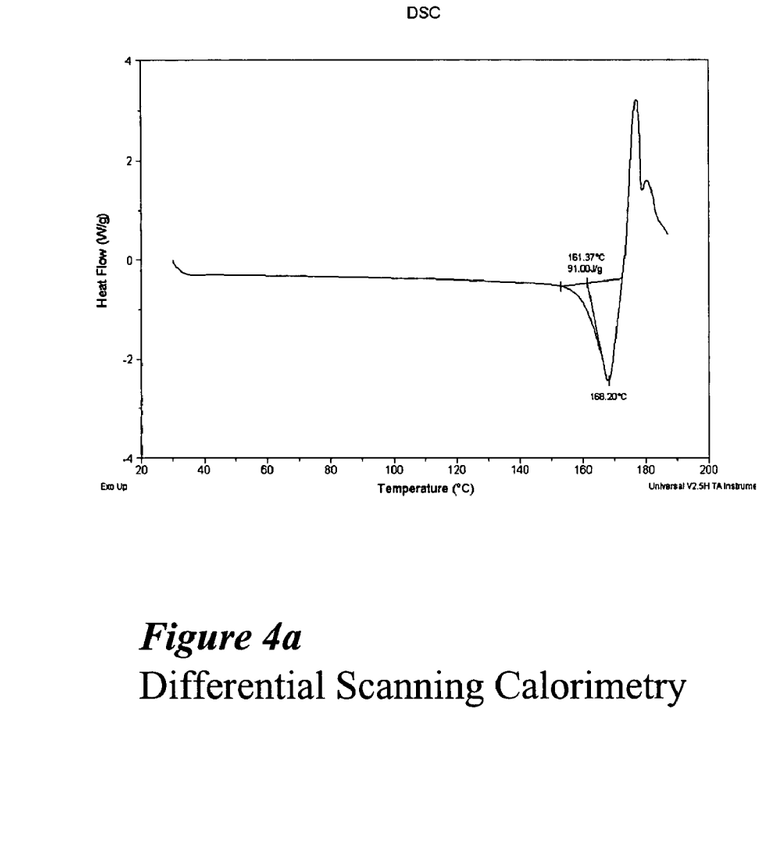
FIG. 4 shows the differential scanning calorimetry (DSC) trace and the thermal gravimetic analysis (TGA) trace of the Form A polymorphic form of Ib.
Figure 4B:
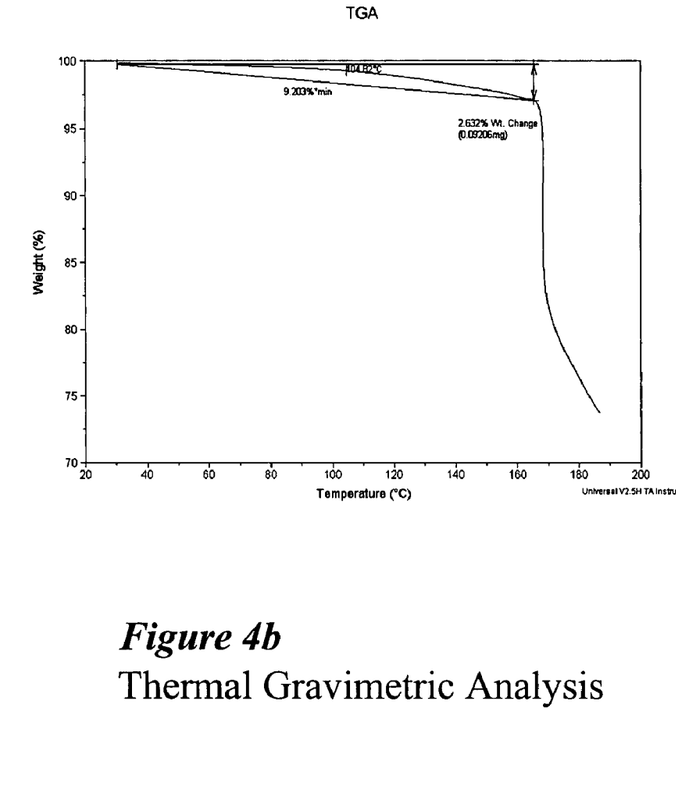

The DSC (Differential Scanning Calorimetry) thermogram shows one endotherm at 161° C. associated with the melt of Form A (FIG. 4A). Thermal gravimetric analysis (TGA) records changes in the mass of a sample as temperature is varied. Form shows a weight loss of 2.6% from 30 to 160° C. (FIG. 4B) corresponding to approximately one half mole of water during the heating phase.

Vapor sorption analysis was used to assess the hygroscopicity of the Form A polymorph. The experiment was run in an isothermal mode and the sample weight recorded as the relative humidity was varied. During the adsorption phase Ib gained 0.5 wt % between 5% relative humidity (RH) and 85% RH. There was less than a 2.5 weight percent increase between 85% and 95% RH. During the desorption phase virtually all of the weight gained in the adsorption phase was lost over the same %RH ranges. These results indicate that the sample is not hygroscopic. At the end of the analysis the sample was still solid and appeared to be crystalline. After the TGA analysis a portion of the sample was recovered and analyzed by DSC. The DSC thermograms of the starting material and of the material recovered following vapor sorption analysis were superimposable. These results indicate that the sample is stable and non-hygroscopic under the experimental conditions.

The exceptional stability of the Form A polymorph of Ib was confirmed in a long-term accelerated stability study to evaluate the effect of temperature, humidity, and light on the quality of the drug substance with time. Stability samples were evaluated for appearance, water content, chemical stability using an HPLC method and physical stability using DSC, specific rotation and x-ray powder diffraction methods. Photochemical stability was assessed by comparison with a control sample that was wrapped in aluminum foil and set side by side with the light sample in the light chamber. Results of the study are contained in Table 2

TABLE 5

Accelerated Stability Study (Form A)

| Storage Condition | Storage Time | Appearance | % Purity (ext. std)[2] | DSC | % Water | Specific Rotation |
|---|---|---|---|---|---|---|
| RT | Initial | White crystalline powder | 98.1 | Onset temp 159.0° C. | 2.25 | 6.3 |
| 2–8° C. | 4 weeks | White crystalline powder | 100.4 | Onset temp 163.17° C. | 2.56 | 8.5 |
| | 3 months | White to off-white crystalline powder | 99.9 | Onset temp 159.90° C. | 2.60 | 8.0 |
| 25° C. 60% RH | 4 weeks | White crystalline powder | 100.2 | Onset temp 162.99° C. | 2.33 | 7.6 |
| | 3 months | White to off-white crystalline powder | 99.8 | Onset temp 159.28° C. | 2.63 | 6.4 |
| 30° C. | 4 weeks | White crystalline | 100.7 | Onset temp | 2.49 | 8.0 |

TABLE 5-continued

Accelerated Stability Study (Form A)

| Storage Condition | Storage Time | Appearance | % Purity (ext. std)[2] | DSC | % Water | Specific Rotation |
|---|---|---|---|---|---|---|
| 60% RH | | powder | | 163.78° C. | | |
| | 3 months | White to off-white crystalline powder | 100.2 | Onset temp 161.55° C. | 2.51 | 7.1 |
| 40° C. 75% RH | 4 weeks | White crystalline powder | 100.6 | Onset temp 161.90° C. | 2.50 | 8.7 |
| | 3 months | White to off-white crystalline powder | 100.1 | Onset temp 160.06° C. | 2.63 | 7.3 |
| 60° C. | 4 weeks | White crystalline powder | 100.8 | Onset temp 160.47° C. | 2.52 | 6.9 |
| | 3 months | White to off-white crystalline powder | 98.7 | Onset temp 159.80° C. | 2.63 | 7.4 |
| Light[1] | ICH Q1B[1] | White crystalline powder | 100.9 | Onset temp 161.88° C. | 2.52 | 7.1 |
| Light Control | ICH Q1B[1] | White crystalline powder | 100.9 | Onset temp 159.38° C. | 2.48 | 7.0 |

[1]International Conference on Harmonization, Bracketing and Matrixing Designs for Stability Testing of Drug Substances and Drug Products (corrected for water and residual solvents).

Over the course of the study Ib the appearance remained consistent with a white crystalline powder. There was no discernable change in the DSC thermograms, specific rotation, water content, x-ray diffraction pattern and purity over the study period for all storage conditions.

Figure 3B:
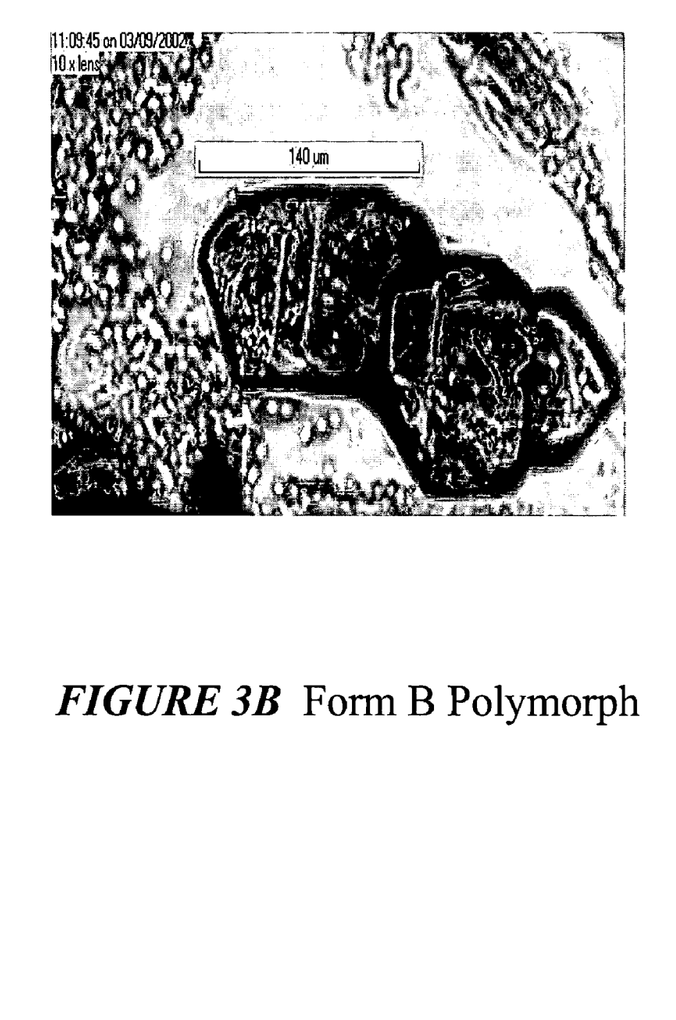
Figure 5A:
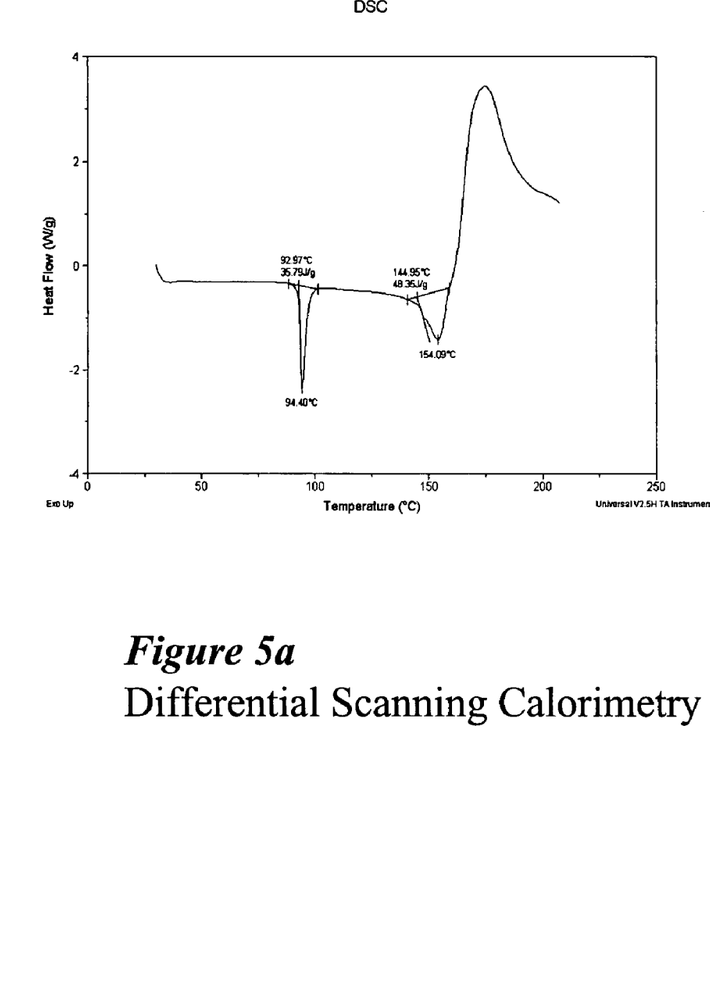
FIG. 5 shows the differential scanning calorimetry (DSC) trace and the thermal gravimetic analysis (TGA) trace of the Form B polymorphic form of Ib.
Figure 5B:
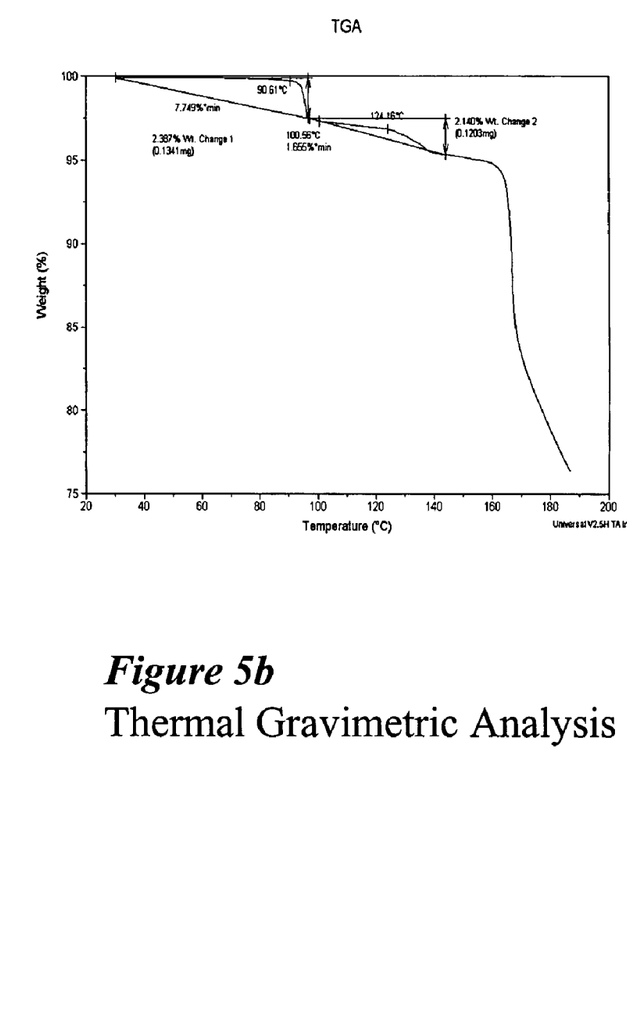

The Form B-polymorph was crystallized from water and formed platelets (FIG. 3B). Form B was physically stable at ambient temperature, 25° C./60% RH, 30° C./60% RH, 40° C./75% RH, and at least 4 weeks. The powder x-ray diffraction pattern is shown in FIG. 1 and the values are tabulated in Table 6. The DSC thermogram shows two endotherms, one at 93° C. and the other at 144.5° C. associated with melt of Form B (FIG. 5A). TGA analysis shows a total weight loss of 4.5% from 30 to 144° C. (FIG. 5B) corresponding to approximately one mole of water per mole of Ib.

TABLE 6

| degrees | D-space | relative intensity | degrees | D-space | relative intensity |
|---|---|---|---|---|---|
| 8.5794 | 10.2980 | 10.45 | 21.3469 | 4.1589 | 9.28 |
| 8.9531 | 9.8689 | 18.94 | 21.8194 | 4.0699 | 16.00 |
| 10.6575 | 8.2942 | 25.69 | 21.1600 | 4.0081 | 31.11 |
| 12.0494 | 7.3390 | 42.22 | 22.3752 | 3.9085 | 15.57 |
| 12.9806 | 6.8145 | 34.08 | 23.5886 | 3.7685 | 7.45 |
| 13.1706 | 6.7166 | 12.12 | 23.9381 | 3.7143 | 50.33 |
| 13.7269 | 6.4457 | 17.68 | 24.1513 | 3.6820 | 20.70 |
| 14.6112 | 6.0572 | 44.64 | 23.0294 | 3.4204 | 58.91 |
| 1577.12 | 5.6425 | 100.0 | 26.4688 | 3.3646 | 16.29 |
| 17.1413 | 5.1687 | 23.52 | 26.9450 | 3.3062 | 47.28 |
| 17.9112 | 4.9482 | 17.84 | 28.0063 | 3.1833 | 8.96 |
| 18.6325 | 4.7582 | 17.84 | 29.7938 | 2.9963 | 16.70 |
| 19.3525 | 4.5828 | 32.87 | 31.5537 | 2.8330 | 14.21 |
| 20.0156 | 4.4324 | 24.86 | 34.9362 | 2.5661 | 13.90 |
| 20.5063 | 4.3275 | 34.15 | 35.2750 | 2.5422 | 13.65 |

Figure 6:
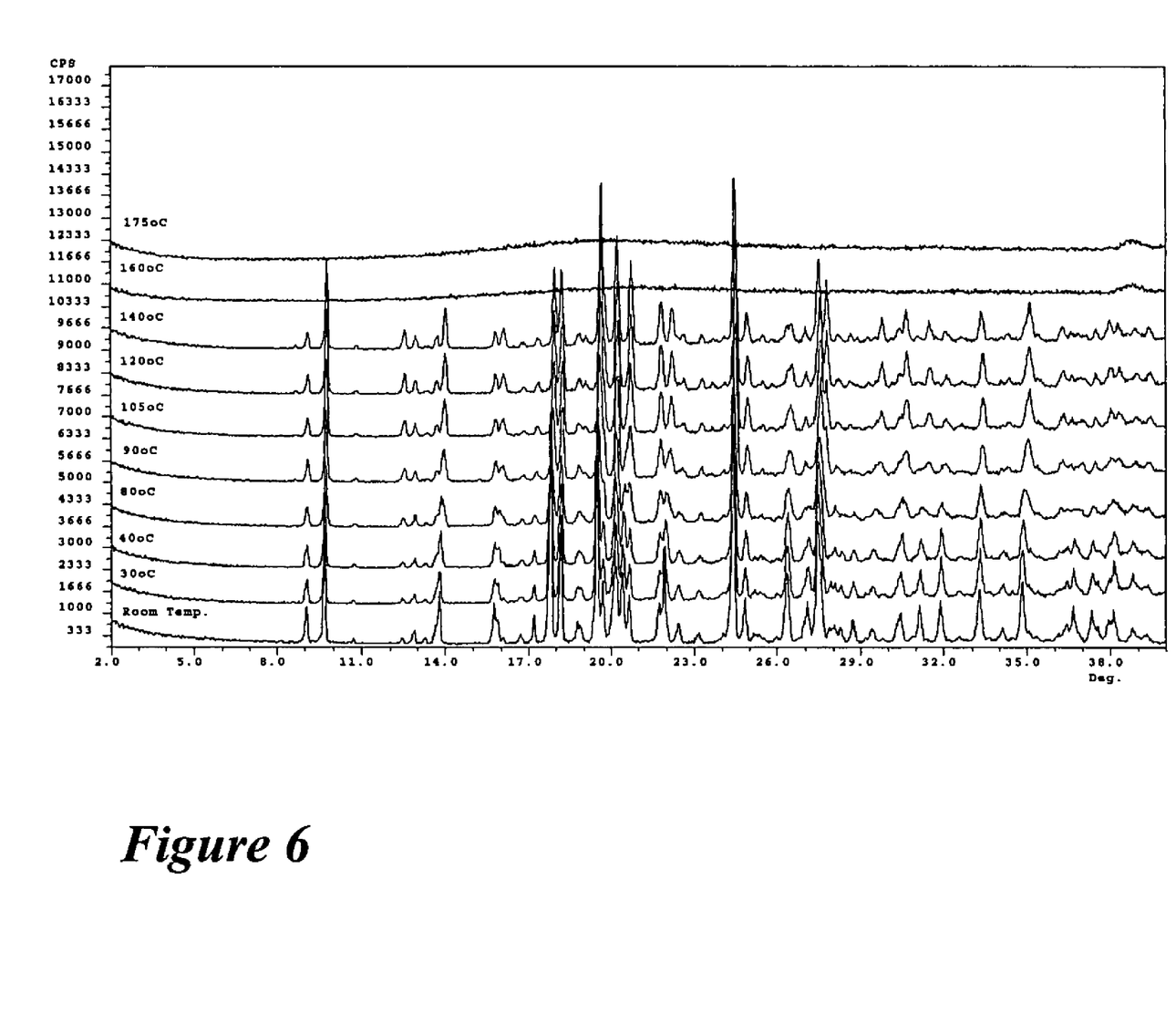
FIG. 6 shows the temperature modulated Powder x-ray diffraction patterns of Form A polymorphic crystalline forms of Ib.
Figure 7:
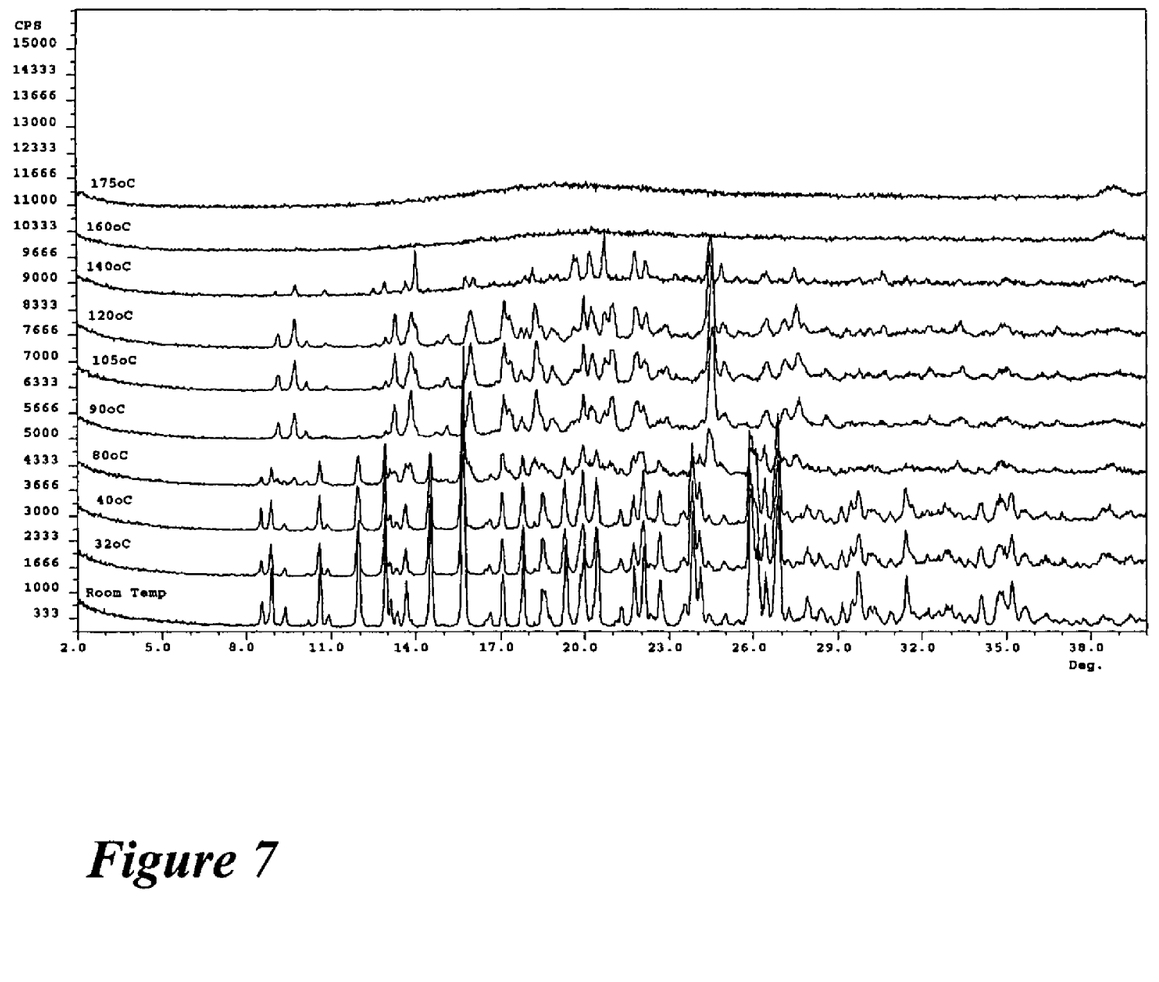
FIG. 7 shows the temperature modulated Powder x-ray diffraction patterns of Form B polymorphic crystalline forms of Ib.

The thermal stability of Form A and Form B was investigated by heating each polymorph from room temperature to 175° C. on modulated temperature x-ray diffractometer. Powder patterns for Form A and Form B are shown in FIGS. 6A and 6B respectively. Form A did not change its crystalline form on heating from room temperature to 175° C. Form B, however, proved unstable and was converted into Form A when the temperature was raised above 80° C. Heating and cooling Form B from 32° C. to 140° C. resulted in conversion of Form B into Form A. Vacuum drying at elevated temperature resulted in conversion of Form B to Form A; however, Form B was stable when subjected to vacuum drying in the absence of heat.

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The term "solvate" as used herein means a compound of the invention or a salt, thereof, that further includes a stoichiometric or non-stoichiometric amount of a solvent bound by non-covalent intermolecular forces.

The term "hydrate" as used herein means a compound of the invention or a salt thereof, that further includes a stoichiometric or non-stoichiometric amount of water bound by non-covalent intermolecular forces. Hydrates are formed by the combination of one or more molecules of water with one molecule of the substances in which the water retains its molecular state as $H_2O$, such combination being able to form one or more hydrate. The term "hemihydrate" as used herein refers to a solid with 0.5 molecule of $H_2O$ per molecule of the substance.

The term "clathrate" as used herein means a compound of the invention or a salt thereof in the form of a crystal lattice that contains spaces (e.g., channels) that have a guest molecule (e.g.), a solvent or water) trapped within.

The term "polymorphs" or "crystal forms" as used herein means crystal structures in which a compound can crystallize in different crystal packing arrangements, all of which have the same elemental composition. Different crystal forms usually have different X-ray diffraction patterns, infrared spectra, melting points, density hardness, crystal shape, optical and electrical properties, stability and solubility. Recrystallization solvent, rate of crystallization, storage temperature, and other factors may cause one crystal form to dominate.

The term "immunomodulator" as used herein means a therapeutic agent that assists in or is capable of modifying or regulating immune functions. An agent that causes an immunological adjustment, regulation or potentiation.

The term "interferon" as used herein means the family of proteins capable of interfering with the viral infection of cells, as well as inhibiting the proliferation of normal and transformed cells, regulating cell differentiation and modulating the immune system. The four major antigenic types of interferon ($\alpha,\beta,\gamma$ and $\omega$) are defined by the cellular source of their production. Type I interferons (interferon $\alpha$, $\beta$, and $\omega$) compete with each other for cellular binding to the type I interferon receptor and thus share at least some components of this multi-subunit cell surface receptor, while the receptor for type II interferon (interferon $\gamma$) is a distinct entity. Both naturally-occurring and recombinant interferons may be administered in combination therapy with compounds of the invention. A consensus sequence for interferon has been described in U.S. Pat. No. 4,897,471 (Y Stabinsky).

The term "chemically-derivatized interferon" as used herein refers to an interferon molecule covalently linked to a polymer which alters the physical and/or pharmacokinetic properties of the interferon. A non-limiting list of such polymers include polyalkylene oxide homopolymers such as polyethylene glycol (PEG) or polypropylene glycol (PPG), polyoxyethylenated polyols, copolymers thereof and block copolymers thereof, provided that the water solubility of the block copolymers is maintained. One skilled in the art will be aware of numerous approaches to linking the polymer and interferon (for example, see A. Kozlowski and J. M. Harris *J. Control. Release* 2001 72(1-3):217-24; C. W. Gilbert and M. Park-Cho, U.S. Pat. No. 5,951,974). A non-limiting list of chemically derivatized IFN$\alpha$ contemplated in the present patent include PEG-interferon-$\alpha$-2a (PEGASYS®) and PEG-interferon-$\alpha$-2b (PEGINTRON™).

Formulations and Administration

Formulations of polymorphic forms of formula I may be prepared by processes known in pharmaceutics art. The following examples (infra) are given to enable those skilled in the art to more clearly understand and to practice the present invention. They should not be considered as limiting the scope of the invention, but merely as being illustrative and representative thereof.

The polymorphic salts of the present invention can be administered in a variety of oral and parenteral dosage forms. Oral dosage forms can be tablets, coated tablets, dragees, hard and soft gelatin capsules, solutions, emulsions, syrups, or suspensions. Parenteral administration includes intravenous, intramuscular, intracutaneous, subcutaneous, intraduodenal, or intraperitoneal administration. Additionally, the salts of the present invention can be administered by transdermal (which may include a penetration enhancement agent), buccal, nasal and suppository routes.

For preparing pharmaceutical compositions from the compounds of the present invention, pharmaceutically acceptable carriers can be either solid or liquid. Solid form preparations include powders, tablets, pills, hard and soft gelatine capsules, cachets, dragees, suppositories, and dispersible granules. A solid carrier can be one or more substances which may also act as diluents, flavoring agents, solubilizers, lubricants, suspending agents, binders, preservatives,-tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired.

Suitable excipients for tablets, coated tablets, dragées, and hard gelatin capsules are, for example, lactose, corn starch and derivatives thereof, magnesium carbonate, magnesium stearate, sugar, lactose, pectin, dextrin, starch, gelatin, tragacanth, methylcellulose, sodium carboxymethylcellulose, talc, and fatty acids or their salts, e.g., stearic acid. If desired, the tablets or capsules may be enteric-coated or sustained release formulations. Suitable excipients for soft gelatine capsules are, for example, vegetable oils, waxes, fats, semi-solid and liquid polyols.

Liquid form preparations include solutions, suspensions, retention enemas, and emulsions, for example water or water/propylene glycol solutions. For parenteral injection, liquid preparations can be formulated in solution in water or water/polyethylene glycol solution.

Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents. Suitable excipients for solutions and syrups for enteral use are, for example, water, polyols, saccharose, invert sugar and glucose. Suitable excipients for injection solutions are, for example, water, saline, alcohols, polyols, e.g., polyalkylene glycols, glycerine or vegetable oils.

Compositions also may contain, in addition to the active component, colorants, flavors, stabilizers, buffers, artificial and natural sweeteners, dispersants, thickeners, solubilizing agents, preservatives, wetting agents, emulsifiers, salts for adjustment of the osmotic pressure, masking agents, antioxidants and the like.

Because the compounds of the present invention are water soluble, they can be administered intravenously in physiological saline solution (e.g., buffered to a pH of about 7.2 to 7.5). Conventional buffers such as phosphates, bicarbonates or citrates can be used in the present compositions.

Also included are solid form preparations which are intended to be converted, shortly before use, to liquid form preparations for oral administration. Such liquid forms include solutions, suspensions, and emulsions.

For preparing suppositories suitable excipients include natural and hardened oils, waxes, fatty acid glycerides, semi-liquid or liquid polyols. The molten homogenous mixture is then poured into convenient sized molds, allowed to cool, and thereby to solidify.

Suitable pharmaceutical carriers, excipients and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in Examples 7-9.

The dosage can vary within wide limits and will, of course, be adjusted in each particular case to the individual requirements of the patient and the severity of the condition being treated. A typical preparation will contain from about 5% to about 95% active compound (w/w). For oral administration, a daily dosage of between about 0.01 and about 100 mg/kg body weight per day should be appropriate in monotherapy and/or in combination therapy. A preferred daily dosage is between about 0.1 and about 300 mg/kg body weight, more preferred 1 and about 100 mg/kg body weight and most preferred 1.0 and about 50 mg/kg body weight per day. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. The daily dosage can be administered as a single dosage or in divided dosages, typically between 1 and 5 dosages per day.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The nucleoside derivatives or the medicaments thereof may be used in monotherapy or combination therapy, i.e. the treatment may be in conjunction with the administration of one or more additional therapeutically active substance(s), for example, an immune system modulator such as an interferon, interleukin, tumor necrosis factor or colony stimulating factor or an anti-inflammatory agent and/or an antiviral agent. When the treatment is combination therapy, such administration may be concurrent or sequential with respect to that of the nucleoside derivatives. Concurrent administration, as used herein thus includes administration of the agents at the same time or at different times. The pharmaceutical composition may optionally contain other therapeutically active agents known in the art.

The references herein to treatment extend to prophylaxis of Hepatitis C mediated diseases as well as to the treatment of existing conditions. Furthermore, treatment of Hepatitis C Virus (HCV) infection, as used herein, also includes treatment or prophylaxis of a disease or a condition associated with or mediated by Hepatitis C Virus (HCV) infection, or the clinical symptoms thereof.

The nucleoside derivatives or the medicaments thereof may be used in monotherapy or combination therapy, i.e. the treatment may be in conjunction with the administration of one or more additional therapeutically active substance(s), for example, an immune system modulator such as an interferon, interleukin, tumor necrosis factor or colony stimulating factor; another anti-viral agent or an anti-inflammatory agent. When the treatment is combination therapy, such administration may be concurrent or sequential with respect to that of the 4'-substituted nucleoside derivatives. Concurrent administration, as used herein thus includes administration of the agents at the same time or at different times.

Preparation of Polymorphic Forms

The preparation of I was described Dvorak et al (provisional patent application filed herewith) which is herein incorporated by reference in its entirety.

EXAMPLE 1

Form A Polymorph

Levovirin valinate hydrochloride (Ib; 75 gm) was warmed to 65° C. in 1.2 L of iso-propanol, and 85 mL of water to produce a homogenous solution This solution was slowly cooled to room temperature and the resulting slurry was filtered, washed with iso-propanol and dried to yield 71 g of the Form A polymorph (m.p. 163-165° C.). (Optionally 4.5 mL of 37% hydrochloric acid can be added to the aqueous iso-propanol solution).

EXAMPLE 2

Form B Polymorph

Levovirin valinate hydrochloride (Ib; 2.8 g) was dissolved in 4 mL of water (saturated solution) and cooled to 2 to 4° C. or lower. After at least three days crystalline plates were recovered by filtration, washed with cold water and dried in vacuo to yield ~2 g of Form B polymorph (m.p. 144° C.; decomposition).

EXAMPLE 3

Bulk and Tap Density

The bulk density of Ib was determined Vanderkamp™ tap density tester, with an acoustic cabinet, or equivalent (Van-Kel Industries, Inc., 36 Meridian Road, Edison, N.J. 08820) apparatus following. Ib was passed through a 20 mesh. A powder funnel was placed on top of a cylinder and the powder was transferred rapidly in to the cylinder while avoiding agitation or tapping of the cylinder and the lower funnel. The sample weight in the cylinder was determined and the bulk density was calculated.

The tapped density was determined by measuring the volume of drug substance in a 25 mL graduated cylinder after 300 taps of a known amount of drug substance. The apparatus used was a VanderKamp Tapped Density Tester. The tapped density was calculated as the known weight of drug substance divided by the measured volume.

EXAMPLE 4

X-Ray Powder Pattern

The X-ray powder diffraction patterns of samples of the polymorphic crystals were measured on a Scintag X1 powder X-ray diffractometer equipped with a sealed copper $K\alpha_1$ irradiation source. The samples were scanned from 2° to 40° 2 θ at a rate of 3° per minute with incident beam slit widths of 4 and 2 microns and diffracted beam slit widths of 0.5 and 0.2 microns.

EXAMPLE 5

Single crystal X-Ray Diffraction

Crystallization

The Form A polymorph was crystallized from iso-propanol, water and 37% hydrochloric acid. Ib was dissolved in the water and the solution was warmed to 45° C. After dilution with the isopropanol, the solution was cooled to ambient temperature and the hydrochloric acid was added. One small particle of Ib was added. The mixture was not stirred. After several hours a solid crystallized from the solution. Without stirring, the mixture was warmed in a water bath to 45° C. The mixture was then allowed to cool overnight while the flask remained immersed in a water bath. The operation above was repeated in a 30° C. bath. The mixture was then allowed to stand at ambient temperature for two days. The supernatant was decanted from the crystalline mass. A 20 mL portion of 15% aqueous iso-propanol was added to the flask, swirled to wash the solid, and then decanted. The procedure was repeated with 20 mL of iso-propanol. The crystalline mass was carefully removed from the flask and was vacuum dried at ambient temperature.

Data Collection and Analysis

A colorless crystal of approximate dimensions 0.29×0.30×0.37 mm was mounted on a glass fiber and transferred to a Bruker CCD platform diffractometer. The SMART (SMART Software Users Guide, Version 5.1, Bruker Analytical X-Ray Systems, Inc.; Madison, Wis. 1999) program package was used to determine the unit-cell parameters and for data collection (25 sec/frame scan time for a sphere of diffraction data). The raw frame data was processed using SAINT (SAINT Software Users Guide, Version 6.0, Bruker Analytical X-Ray Systems, Inc.; Madison, Wis. 1999) and SADABS (Sheldrick, G. M. SADABS Version 2.05, Bruker Analytical X-Ray Systems, Inc.; Madison, Wis. 2001) to yield the reflection data file. Subsequent calculations were carried out using the SHELXT program (Sheldrick, G. M. SHELXTL Version 6.12, Bruker Analytical X-Ray Systems, Inc.; Madison, Wis. 2001). The diffraction symmetry was 2/m and the systematic absences were consistent with the monoclinic space groups $P2_1$ and $P2_1/m$. It was later determined that the noncentrosymmetric space group $P2_1$ was correct.

The structure was solved by direct methods and refined on $F^2$ by full-matrix least-squares techniques. The analytical scattering factors (International Tables for X-Ray Crystallography 1992, Vol. C., Dordrecht: Kluwer Academic Publishers) for neutral atoms were used throughout the analysis. Hydrogen atoms were located from a difference-Fourier map and refined (x, y, z and $U_{iso}$). There were two molecules of the formula unit present (Z=4). There was also one-half molecule of water per formula unit.

At convergence, wR2=0.0740 and GOF=1.038 for 644 variables refined against 8138 data. As a comparison for refinement on F, R1=0.0294 for those 7740 data with I>2.0σ (I). The absolute structure was assigned by refinement of the Flack parameter (H. D. Flack *Acta. Cryst.*, 1983 A39:876-8810. Crystal data and structure refinement are summarized in Table 7.

TABLE 7

| Empirical formula | $C_{13}H_{22}ClN_5O_6 \cdot \frac{1}{2}(H_2O)$ |
|---|---|
| Formula weight | 388.81 |
| Temperature | 163(2) K |
| Wavelength | 0.71073 Å |
| Crystal system | Monoclinic |
| Space group | $P2_1$ |
| Unit cell dimensions | a = 9.0728(4) Å    α = 90° |
| | b = 19.2932(8) Å    β = 90.6020(10)° |
| | c = 10.2240(4) Å    γ = 90° |
| Volume | 1789.54(13) Å$^3$ |
| Z | 4 |
| Density (calculated) | 1.443 Mg/m$^3$ |
| Absorption coefficient | 0.257 mm$^{-1}$ |
| F(000) | 820 |
| Crystal size | 0.37 × 0.30 × 0.29 mm$^3$ |
| Theta range for data collection | 1.99 to 28.28°. |
| Index ranges | −12 ≤ h ≤ 11, −24 ≤ k ≤ 24, −13 ≤ l ≤ 13 |
| Reflections collected | 18196 |
| Independent reflections | 8138 [R(int) = 0.0217] |
| Completeness to theta = 28.28° | 96.4% |
| Absorption correction | semi-empirical from equivalents |
| Max. and min. transmission | 0.9291 and 0.9108 |
| Refinement method | Full-matrix least squares on F$^2$ |
| Data/restraints/parameters | 8138/1/644 |
| Goodness-of-fit on F$^2$ | 1.038 |
| R indices [I > 2sigma(I)] | R1 = 0.0294, wR2 = 0.0725 |
| R indices (all data) | R1 = 0.0317, wR2 = 0.0740 |
| Absolute structure parameter | −0.03(3) |
| Largest diff. peak and hole | 0.793 and −0.179 e.Å$^{-3}$ |

EXAMPLE 6

Thermochemical Analysis

DSC Thermograms were collected using a 2920 Modulated DSC from Thermal Analyzer (TA) Instruments. The heating rate was 10° C./min with a nitrogen purge maintained throughout the run.

Thermogravimetric analysis was conducted using a Hi-Res 2950 TGA (TA Instruments). The sample was heated from 30° C. to 280° C. at a rate of 10° C./min and a nitrogen flow was maintained throughout each run.

EXAMPLE 7

Vapor Sorption Analysis

A 0.026 g sample of Ib (Form A) was exposed to a cyclic program of 5%-95%-5% Relative Humidity (RH) using a SGA-100 Symmetric Vapor Sorption Analyzer (VTI). The experimental protocol was set up to dry the sample at 60° C. for a maximum of 1 h or until an equilibrium condition was reached which fluctuated less then 0.02 wt % in 5 min. The experiment was run isothermally at 25° C., and the %RH was increased from 5% to 95% in 10% increments. After each increment the sample held constant until equilibrium was reached. Equilibrium was defined as a per cent weight change of not more than 0.005 wt % in 5.00 minutes. After reaching 95% RH the RH was lowered back to 5% RH. If equilibrium was not reached within 2 hours, the %RH was advanced to the next programmed level.

EXAMPLE 8

HPLC Analytical Methodology

HPLC grade deionized water obtained from Milli-Q Water Purification System (Millipore Corp., Milford Mass.), HPLC grade acetonitrile (Burdick Jackson Lab, Inc., Muskegon, Mich.), -Heptane sulfonic acid sodium salt, monohydrate (Fluka), Phosphoric acid, 85% (Mallinckrodt, Sigma, or Fluka), and Hydrochloric Acid, 1 N (J. T. Baker) were used to prepared mobile phase and dilution solvent.

Chromatography was carried out on a Zorbax SB-CN, 4.6×150 mm, 3.5 µm column. A ternary solvent gradient was used comprised of (A) water, (B) acetonitrile and (C) 200 mM heptane sulfonic acid sodium salt, monohydrate with 1% phosphoric acid in water. To prepare 500 mL of the solution, dissolve 22.0 g of 1-heptane sulfonic acid sodium salt, monohydrate in about 400 mL of water. Add 5 mL of phosphoric acid, 85% and then dilute to a volume of 500 mL with water and mix thoroughly. A flow rate of 1.0 mL/m was used. The column was run isocratically with 90% A and 10% C for 5 m. A linear gradient to 20% A, 70% B and 10% C was run over 20 m. This mixture was run isocratically for an addition 5 m after which the solvent was ramped back to 90% A and 10% B over 2 m followed by 8 m to reequilibrate the column. The column was maintained at 40° C. The retention time of Ib was approximately 11 m.

EXAMPLE 9

Representative Formulations

| COMPOSITION FOR ORAL ADMINISTRATION | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| COMPOSITION FOR ORAL ADMINISTRATION | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| COMPOSITION FOR ORAL ADMINISTRATION | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 mL |
| Colorings | 0.5 mg |
| Distilled water | q.s. to 100 mL |

The ingredients are mixed to form a suspension for oral administration.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A polymorphic hemihydrate crystalline form (Form A) of a compound according to formula Ib with an x-ray powder diffraction trace having D-spacing essentially as shown:

(Ib)

| D-space | $I/I_o \times 100$ |
|---|---|
| 9.1200 | 35.42 |
| 6.4204 | 39.48 |
| 5.6103 | 33.43 |
| 4.9820 | 68.77 |
| 4.8788 | 41.38 |
| 4.5547 | 66.82 |
| 4.5098 | 36.84 |
| 4.4227 | 55.89 |
| 4.3497 | 43.98. |
| 4.3019 | 35.58 |
| 4.0573 | 50.71 |
| 3.7012 | 100.0 |
| 3.5856 | 34.16 |
| 3.3832 | 53.52 |
| 3.2480 | 48.14 |
| 2.6876 | 40.44 |
| 2.5744 | 26.15. |

2. A polymorphic hemihydrate crystalline form (Form A) of a compound according to claim 1 with an single crystal x-ray atomic coordinates essentially as listed in Table 4.

TABLE 4

Atomic coordinates (x $10^4$) and equivalent isotropic displacement parameters ($Å^2$x $10^3$) for Form A of 1b.

| | x | y | z | U(eq) | | x | y | z | U(eq) |
|---|---|---|---|---|---|---|---|---|---|
| Cl(1) | 8746(1) | 8772(1) | 3214(1) | 29(1) | Cl(2) | 4337(1) | 7796(1) | 2768(1) | 25(1) |
| C(1) | 8687(2) | 7008(1) | 6432(2) | 18(1) | C(14) | 11235(2) | 8965(1) | −1389(2) | 17(1) |
| C(2) | 8690(2) | 7291(1) | 5035(2) | 17(1) | C(15) | 11243(2) | 8693(1) | 16(2) | 17(1) |

TABLE 4-continued

Atomic coordinates (x $10^4$) and equivalent isotropic displacement parameters ($Å^2$x $10^3$) for Form A of 1b.

| | x | y | z | U(eq) | | x | y | z | U(eq) |
|---|---|---|---|---|---|---|---|---|---|
| C(3) | 8434(2) | 6632(1) | 4217(2) | 19(1) | C(16) | 10963(2) | 9359(1) | 810(2) | 17(1) |
| C(4) | 9276(2) | 6098(1) | 5024(2) | 19(1) | C(17) | 11762(2) | 9898(1) | −1(2) | 17(1) |
| C(5) | 4955(2) | 7249(1) | 7211(2) | 18(1) | C(18) | 7490(2) | 8857(1) | −2164(2) | 17(1) |
| C(6) | 6915(2) | 7088(1) | 8326(2) | 18(1) | C(19) | 9413(2) | 8859(1) | −3274(2) | 19(1) |
| C(7) | 3358(2) | 7239(1) | 6862(2) | 19(1) | C(20) | 5898(2) | 8825(1) | −1815(2) | 17(1) |
| C(8) | 8850(2) | 5352(1) | 4814(2) | 24(1) | C(21) | 11261(2) | 10634(1) | 179(2) | 21(1) |
| C(9) | 6719(2) | 4664(1) | 5104(2) | 18(1) | C(22) | 9088(2) | 11295(1) | −17(2) | 18(1) |
| C(10) | 5057(2) | 4711(1) | 5279(2) | 18(1) | C(23) | 7418(2) | 11254(1) | −138(2) | 17(1) |
| C(11) | 4573(2) | 5165(1) | 6448(2) | 21(1) | C(24) | 6847(2) | 10747(1) | −1189(2) | 20(1) |
| C(12) | 4725(2) | 4773(1) | 7744(1) | 30(1) | C(25) | 5164(1) | 10780(1) | −1296(2) | 26(1) |
| C(13) | 3010(2) | 5434(1) | 6239(2) | 26(1) | C(26) | 7564(2) | 10867(1) | −2511(2) | 30(1) |
| O(1) | 9023(1) | 6287(1) | 6364(1) | 22(1) | O(7) | 11560(1) | 9687(1) | −1339(1) | 19(1) |
| O(2) | 10098(1) | 7585(1) | 4803(1) | 22(1) | O(8) | 12683(1) | 8438(1) | 289(1) | 20(1) |
| O(3) | 8995(2) | 6642(1) | 2942(1) | 27(1) | O(9) | 11606(1) | 9330(1) | 2076(1) | 21(1) |
| O(4) | 2417(1) | 7239(1) | 7729(1) | 27(1) | O(10) | 4940(1) | 8842(1) | −2681(1) | 24(1) |
| O(5) | 7272(1) | 5301(1) | 5010(1) | 28(1) | O(11) | 9666(1) | 10660(1) | 22(1) | 22(1) |
| O(6) | 7405(1) | 4136(1) | 5026(1) | 22(1) | O(12) | 9772(1) | 11826(1) | 60(1) | 24(1) |
| N(1) | 7250(1) | 7087(1) | 7046(1) | 17(1) | N(6) | 9782(1) | 8878(1) | −1997(1) | 17(1) |
| N(2) | 5989(2) | 7123(1) | 6315(1) | 18(1) | N(7) | 8543(2) | 8882(1) | −1263(I) | 19(1) |
| N(3) | 5467(2) | 7117(1) | 8473(1) | 19(1) | N(8) | 7968(2) | 8845(1) | −3432(1) | 20(1) |
| N(4) | 3060(1) | 7314(1) | 5602(1) | 23(1) | N(9) | 5625(2) | 8781(1) | −549(1) | 24(1) |
| N(5) | 4480(2) | 3990(1) | 5347(1) | 17(1) | N(10) | 6858(2) | 11973(1) | −323(1) | 18(1) |
| | | | | | O(13) | 7403(2) | 7598(1) | 1411(2) | 42(1). |

3. A process for preparing a Form A polymorph of claim 1 comprising crystallizing the compound (Ib) from iso-propanol and water optionally containing hydrochloric acid.

4. A polymorphic crystalline form of a compound according to formula Ib prepared in accordance with the process of claim 3.

5. A method of treating Hepatitis C Virus comprising administering to a patient having Hepatitis C a therapeutically effective amount of a Form A polymorph according to claim 1.

6. The method of claim 5 further comprising administering an immune system modulator or an antiviral compound.

7. The method of claim 6 wherein the immune system modulator is interferon or a chemically derivatized interferon.

8. A pharmaceutical composition comprising the Form A polymorph according to claim 1 in admixture with at least one pharmaceutically acceptable carrier, diluent or excipient.

9. A polymorphic crystalline form (Form B) of a compound according to formula Ib 1 with an x-ray powder diffraction trace having D-spacing essentially as shown:

(Ib)

| D-space | I/I$_o$ x 100 |
|---|---|
| 9.8689 | 18.94 |
| 8.2942 | 25.69 |
| 7.3390 | 42.22 |
| 6.8145 | 34.08 |

-continued (Ib)

| D-space | I/I$_o$ x 100 |
|---|---|
| 6.0572 | 44.64 |
| 5.6245 | 100.0 |
| 5.1887 | 23.52 |
| 4.9482 | 22.35 |
| 4.5828 | 32.87 |
| 4.4324 | 24.86 |
| 4.3275 | 34.15 |
| 4.0081 | 31.11 |
| 3.7143 | 50.33 |
| 3.4204 | 58.91 |
| 3.3062 | 47.28. |

10. A process for preparing a Form B polymorph of claim 9 comprising crystallizing the compound (Ib) from water.

11. A polymorphic crystalline form of a compound according to formula Ib prepared in accordance with the process of claim 10.

12. A method of treating Hepatitis C virus comprising administering to a patient having Hepatitis C a therapeutically effective amount of a Form B polymorph according to claim 9.

13. The method of claim 12, further comprising administering an immune system modulator and/or an antiviral compound.

14. The method of claim 13 wherein the immune system modulator is interferon or a chemically derivatized interferon.

15. A pharmaceutical composition comprising the Form B polymorph according to claim 9 in admixture with at least one pharmaceutically acceptable carrier, diluent or excipient.

* * * * *